United States Patent
Mesa et al.

(10) Patent No.: US 7,262,337 B2
(45) Date of Patent: Aug. 28, 2007

(54) METHOD FOR MODIFYING A PLANT PHENOTYPE

(75) Inventors: Jose Ramon Botella Mesa, Kenmore (AU); Joshua Scott Mylne, Kenmore Hills (AU)

(73) Assignee: The University of Queensland, Queensland (AU)

( * ) Notice: Subject to any disclaimer, the term of this patent is extended or adjusted under 35 U.S.C. 154(b) by 248 days.

(21) Appl. No.: 10/433,754

(22) PCT Filed: Dec. 7, 2001

(86) PCT No.: PCT/AU01/01587

§ 371 (c)(1),
(2), (4) Date: Oct. 3, 2003

(87) PCT Pub. No.: WO02/45486

PCT Pub. Date: Jun. 13, 2002

(65) Prior Publication Data

US 2004/0098758 A1  May 20, 2004

(30) Foreign Application Priority Data

Dec. 8, 2000 (AU) .................................. PR 2011

(51) Int. Cl.
*C12N 15/82* (2006.01)
*C12N 5/04* (2006.01)
*A01H 5/00* (2006.01)
*A01H 5/10* (2006.01)

(52) U.S. Cl. ............... 800/278; 800/298; 800/290; 800/287; 800/320; 800/306; 435/419

(58) Field of Classification Search ................ 800/278, 800/298, 290, 320.1, 320, 306; 435/468; 536/23.1, 23.6
See application file for complete search history.

(56) References Cited

FOREIGN PATENT DOCUMENTS

EP  1 033 405  9/2000

OTHER PUBLICATIONS

Kano-Murakami et al (1993, FEBS 334:365-368).*
Newman et al., 1998, NCBI Accession No. T20918.*
Bowie et al, Science 247:1306-1310, 1990.*
McConnell et al, Nature 411 (6838):709-713, 2001.*
Fourgoux-Nicol et al (1999, Plant Molecular Biology 40 :857-872).*
Siegfried et al (1999, Development 126 (18):4117-4128).*

* cited by examiner

*Primary Examiner*—Stuart F. Baum
(74) *Attorney, Agent, or Firm*—Knobbe, Martens, Olson & Bear, LLP

(57) ABSTRACT

The present invention relates generally to methods for generating plants having altered phenotypes, and to plants so generated and parts of these plants. More particularly, the present invention relates to a method for modifying a plant so as to produce a plant exhibiting an altered phenotype. Particularly useful altered phenotypes contemplated by the present invention include plants having altered tissue architecture. The present invention further contemplates genetic sequences capable of facilitating the modification of a phenotype of a plant and to sequences complementary thereto and to derivatives of the sequences. Plants and parts of plants, such as flowering and reproductive parts including seeds, also form part of the present invention. The ability to modify the phenotype of a plant may be useful for, inter alia, producing plants with more highly desired characteristics, such as delayed flowering, increased lateral branching, delayed senescence and the like.

34 Claims, 7 Drawing Sheets

SEQUENCE LISTING

```
<160> NUMBER OF SEQ ID NOS: 2

<210> SEQ ID NO 1
<211> LENGTH: 614
<212> TYPE: DNA
<213> ORGANISM: Arabidopsis thaliana
<220> FEATURE:
<221> NAME/KEY: CDS
<222> LOCATION: (85)..(390)

<400> SEQUENCE: 1
atactctcat atatatttgc atctaatctt gtaagcaaac gttatcactt gtctacacaa      60
```

-continued

```
cattctttca tttacaataa taat atg ggt gta aca tta gaa gga caa aga      111
                          Met Gly Val Thr Leu Glu Gly Gln Arg
                           1               5 aag gaa tca att tgg gtt ttg atg aga aga caa agg gct cga agg gca      159
Lys Glu Ser Ile Trp Val Leu Met Arg Arg Gln Arg Ala Arg Arg Ala
 10              15                  20                  25 ctt gtg aag aag atc atg atc cga cca agg aag agt gta gaa gct tct      207
Leu Val Lys Lys Ile Met Ile Arg Pro Arg Lys Ser Val Glu Ala Ser
                 30                  35                  40 aga aga cct tgt cgc gca ata cac aga cga gtg aag acg cta aaa gag      255
Arg Arg Pro Cys Arg Ala Ile His Arg Arg Val Lys Thr Leu Lys Glu
             45                  50                  55 ctt gtt ccc aac acc aaa aca tca gaa ggt tta gat gga ctc ttt aga      303
Leu Val Pro Asn Thr Lys Thr Ser Glu Gly Leu Asp Gly Leu Phe Arg
         60                  65                  70 caa acg gca gat tat atc ttg gct ttg gaa atg aaa gtg aaa gtt atg      351
Gln Thr Ala Asp Tyr Ile Leu Ala Leu Glu Met Lys Val Lys Val Met
     75                  80                  85 cag aca atg gtt cag gtt ttg acc gaa act aac tgt gtt taaaagcctt       400
Gln Thr Met Val Gln Val Leu Thr Glu Thr Asn Cys Val
 90                  95                 100 catatatttt ttgtatatct tgttggattt tacgttcttt ttagtttta tttgttcgtg     460 tttattttt attatctcgt gtgattgtct tgtgttgctt atatagaaaa ggaatttggt     520
ttatcttgct gctgtagact atgcagaaaa ttaaatatca aaatatata tgtattatat    580 gcttatctaa ataacagatg actgttggtt cggc                                614
```

<210> SEQ ID NO 2
<211> LENGTH: 102
<212> TYPE: PRT
<213> ORGANISM: Arabidopsis thaliana

<400> SEQUENCE: 2

```
Met Gly Val Thr Leu Glu Gly Gln Arg Lys Glu Ser Ile Trp Val Leu
 1               5                  10                  15

Met Arg Arg Gln Arg Ala Arg Arg Ala Leu Val Lys Lys Ile Met Ile
             20                  25                  30

Arg Pro Arg Lys Ser Val Glu Ala Ser Arg Arg Pro Cys Arg Ala Ile
         35                  40                  45

His Arg Arg Val Lys Thr Leu Lys Glu Leu Val Pro Asn Thr Lys Thr
     50                  55                  60

Ser Glu Gly Leu Asp Gly Leu Phe Arg Gln Thr Ala Asp Tyr Ile Leu
 65                  70                  75                  80

Ala Leu Glu Met Lys Val Lys Val Met Gln Thr Met Val Gln Val Leu
                 85                  90                  95

Thr Glu Thr Asn Cys Val
            100
```

METHOD FOR MODIFYING A PLANT PHENOTYPE

This is the U.S. National Phase under 35 U.S.C. § 371 of International Application PCT/AU01/01587, filed Dec. 7, 2001, which claims priority of Australian provisional application No. PR2011/00, filed Dec. 8, 2000. Each of the above applications are incorporated herein by reference in their entirety.

FIELD OF THE INVENTION

The present invention relates generally to methods for generating plants having altered phenotypes, and to plants so generated and parts of these plants. More particularly, the present invention relates to a method for modifying a plant so as to produce a plant exhibiting an altered phenotype. Particularly useful altered phenotypes contemplated by the present invention include plants having altered tissue architecture. The present invention further contemplates genetic sequences capable of facilitating the modification of a phenotype of a plant and to sequences complementary thereto and to derivatives of the sequences. Plants and parts of plants, such as flowering and reproductive parts including seeds, also form part of the present invention. The ability to modify the phenotype of a plant may be useful for, inter alia, producing plants with more highly desired characteristics, such as delayed flowering, increased lateral branching, delayed senescence and the like.

BACKGROUND OF THE INVENTION

Bibliographic details of the publications referred to by author in this specification are collected at the end of the description.

Reference to any prior art in this specification is not, and should not be taken as, an acknowledgment or any form of suggestion that this prior art forms part of the common general knowledge in Australia or any other country.

Recombinant DNA technology is now an integral part of strategies to generate genetically modified eukaryotic cells. The past decade of plant molecular biology has seen the identification and cloning of thousands of genetic sequences, of both genomic and cDNA origin, from hundreds of plant species. With the recent development of advanced rapid techniques for cloning and sequencing and the completion or near-completion of the sequencing of entire genomes, such as for example for *Arabidopsis* and rice, attention has been re-focused on to the characterization of isolated sequences and the elucidation of their in vivo function.

One approach for carrying out these studies involves the production of a range of mutant plant lines exhibiting loss-of-function or gain-of-function phenotypes, and the subsequent selection and characterization of the mutant phenotypes produced. Techniques are available for the genetic transformation of a number of plant species and for the modulation of expression of genetic sequences, such as by the introduction of sense and/or antisense copies of particular genetic sequences.

In recent work leading up to the present invention, the inventors sought to identify modified phenotypes having potential commercial interest. In accordance with the present invention, the inventors have now identified a genetic sequence capable of modification of a plant's tissue architecture. The plants so generated exhibit commercially useful traits.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

The present invention provides a method for generating plants and parts of plants having modified phenotypes. Particularly useful modified phenotypes contemplated by the present invention include plants having altered tissue architecture. Examples of altered tissue architecture include but are not limited to changes in cell shape to create larger more elongated structures, or to create smaller more compact structures; changes in cellular development leading to diversion of developmental pathways and concomitant absence of some tissues; changes in cell numbers leading to smaller or larger tissues, all of which changes ultimately lead to a modified phenotype such as, for example, shorter or longer stem tissue, reduced or increased lateral branching, preferential growth of inflorescence-bearing tissues rather than leaf-bearing tissues, decreased height and increased compactness of plant shape. A phenotype incorporating any one or more of these changes is referred to herein as "plentiful".

The present invention further contemplates genetic sequences capable of facilitating the modification of a phenotype of a plant and to sequences complementary thereto and to derivatives of these sequences. The preferred nucleotide sequence of the present invention is also referred to herein as "plentiful" and comprises the nucleotide sequence as set forth in SEQ ID NO:1. The proteinaceous product of plentiful comprises an amino acid sequence as set forth in SEQ ID NO:2.

Plants and parts of plants, such as flowering and reproductive parts including seeds, also form part of the present invention. The ability to modify the phenotype of a plant may be useful for, inter alia, producing plants with more highly desired characteristics, such as delayed flowering, increased lateral branching, delayed senescence and the like.

Accordingly, one aspect of the present invention contemplates a method for generating a plant with a modified plant phenotype, said method comprising introducing into the genome of one or more cells of a plant or one or more cells of a parent of a first-mentioned plant a nucleic acid molecule which, when expressed in cells of a plant, results in the phenotype of the cells being modified relative to cells not expressing said nucleic acid molecule.

In a particularly preferred embodiment, the present invention contemplates a method for modulating plant tissue architecture, said method comprising introducing into the genome of one or more cells of a plant or one or more cells of a parent of a first-mentioned plant a nucleic acid molecule capable of effecting an alteration to cellular or tissue architecture and then regenerating a plant from said one or more cells.

Another aspect of the present invention is directed to a method for generating a plant with a modified plant phenotype, said method comprising introducing into the genome of one or more cells of said plant or one or more cells of a parent of said first-mentioned plant a nucleic acid molecule comprising a nucleotide sequence encoding or a sequence complementary to a nucleotide sequence encoding an amino acid sequence set forth in SEQ ID NO:2 or a derivative thereof including an amino acid sequence having at least about 75% sequence identity with SEQ ID NO:2 after optimal alignment and then regenerating a plant from said plant cells to produce a plant with said altered phenotype and optionally generating a progeny plant with said altered phenotype from said regenerated plant.

A related aspect of the present invention is directed to a method for facilitating the modification of a plant phenotype, said method comprising introducing into the genome of one or more cells of a said plant or one or more cells of a parent of said first-mentioned plant a nucleic acid molecule comprising a nucleotide sequence homolog encoding or a sequence complementary to a nucleotide sequence encoding an amino acid sequence set forth in SEQ ID NO:2 or a derivative thereof including an amino acid sequence having at least about 75% identity to SEQ ID NO:2 after optimal alignment.

A further aspect of the present invention is directed to a method for altering the phenotype of a plant, said method comprising introducing into the genome of one or more cells of said plant or one or more cells of a parent of said first-mentioned plant a nucleic acid molecule comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

Yet another aspect of the present invention is directed to a method for altering the phenotype of a plant, said method comprising introducing into the genome of one or more cells of a plant or one or more cells of a parent of said first-mentioned plant a chimeric genetic construct comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

Still another aspect of the present invention is directed to a chimeric genetic construct comprising a nucleic acid molecule comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

Even yet another aspect of the present invention is directed to a vector in the form of a chimeric construct comprising a nucleic acid molecule having a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

Another aspect of the present invention provides a method for generating a plant with altered tissue architecture, said method comprising introducing into the genome of one or more cells of said plant or one or more cells of a parent of said first-mentioned plant a nucleic acid molecule comprising a nucleotide sequence encoding or a sequence complementary to a nucleotide sequence encoding an amino acid sequence set forth in SEQ ID NO:2 or a derivative thereof including an amino acid sequence having at least about 75% similarity to SEQ ID NO:2 after optimal alignment and then regenerating a plant from said plant cells to produce a plant with said altered tissue architecture and optionally generating a progeny plant with said altered tissue architecture from said regenerated plant.

In a related aspect, the present invention provides a method for modifying plant tissue architecture, said method comprising introducing into the genome of one or more cells of said plant or one or more cells of a parent of said first-mentioned plant a nucleic acid molecule comprising a nucleotide sequence encoding, or a sequence complementary to a nucleotide sequence encoding, an amino acid sequence set forth in SEQ ID NO:2 or a derivative thereof including an amino acid sequence having at least about 75% identity to SEQ ID NO:2 after optimal alignment.

A further aspect of the present invention contemplates a method for modifying plant tissue architecture, said method comprising introducing into the genome of one or more cells of said plant or one or more cells of a parent of said first-mentioned plant a nucleic acid molecule comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

Yet another aspect of the present invention provides a transfected or transformed cell, tissue, or organ which comprises a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions and/or is capable of producing an amino acid sequence set forth in SEQ ID NO:2 or a derivative thereof including an amino acid sequence having at least about 75% sequence identity with SEQ ID NO:2 after optimal alignment.

Still another aspect of the present invention provides a method for modifying plant tissue architecture, said method comprising introducing into the genome of one or more cells of said plant or one or more cells of a parent of said first-mentioned plant a vector comprising a chimeric genetic construct comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions and then regenerating a plant from said plant cells to produce a plant with modified tissue architecture.

Even still another aspect of the present invention provides a genetically modified plant cell or multicellular plant or progeny thereof or parts of said transgenic plant having an altered phenotype compared to its non-transformed equivalent, wherein said transgenic plant comprises the nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

Even yet another aspect of the present invention contemplates a genetically modified plant cell or multicellular plant or progeny or parts thereof comprising a nucleic acid molecule comprising a nucleotide sequence encoding or a sequence complementary to a sequence encoding an amino acid sequence set forth in SEQ ID NO:2 or a derivative thereof or an amino acid sequence having at least about 75% sequence identity with SEQ ID NO:2 after optimal alignment.

Another aspect of the present invention provides a plant cell or multicellular plant or progeny or parts thereof wherein said cell, plant, progeny or part thereof exhibits altered tissue architecture compared to its non-transformed equivalent.

A further aspect of the present invention is directed to the use of a nucleic acid molecule comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions in the manufacture of a transgenic plant having tissues with altered phenotype.

BRIEF DESCRIPTION OF THE FIGURES

FIGS. 4A and B compare photographic representations of Southern analysis of (FIG. 4A) CaMV35S and (FIG. 4B) plentiful fragment pattern for non-transformed wild-type (WT) and two transformed lines displaying the plentiful phenotype (Lines 4B and 5D), each digested with restriction enzymes EcoRI, HindIII and SalI, as shown. Size markers are also indicated. The results provide evidence for independent transformation events.

DETAILED DESCRIPTION OF THE PREFERRED EMBODIMENTS

Figure 1:
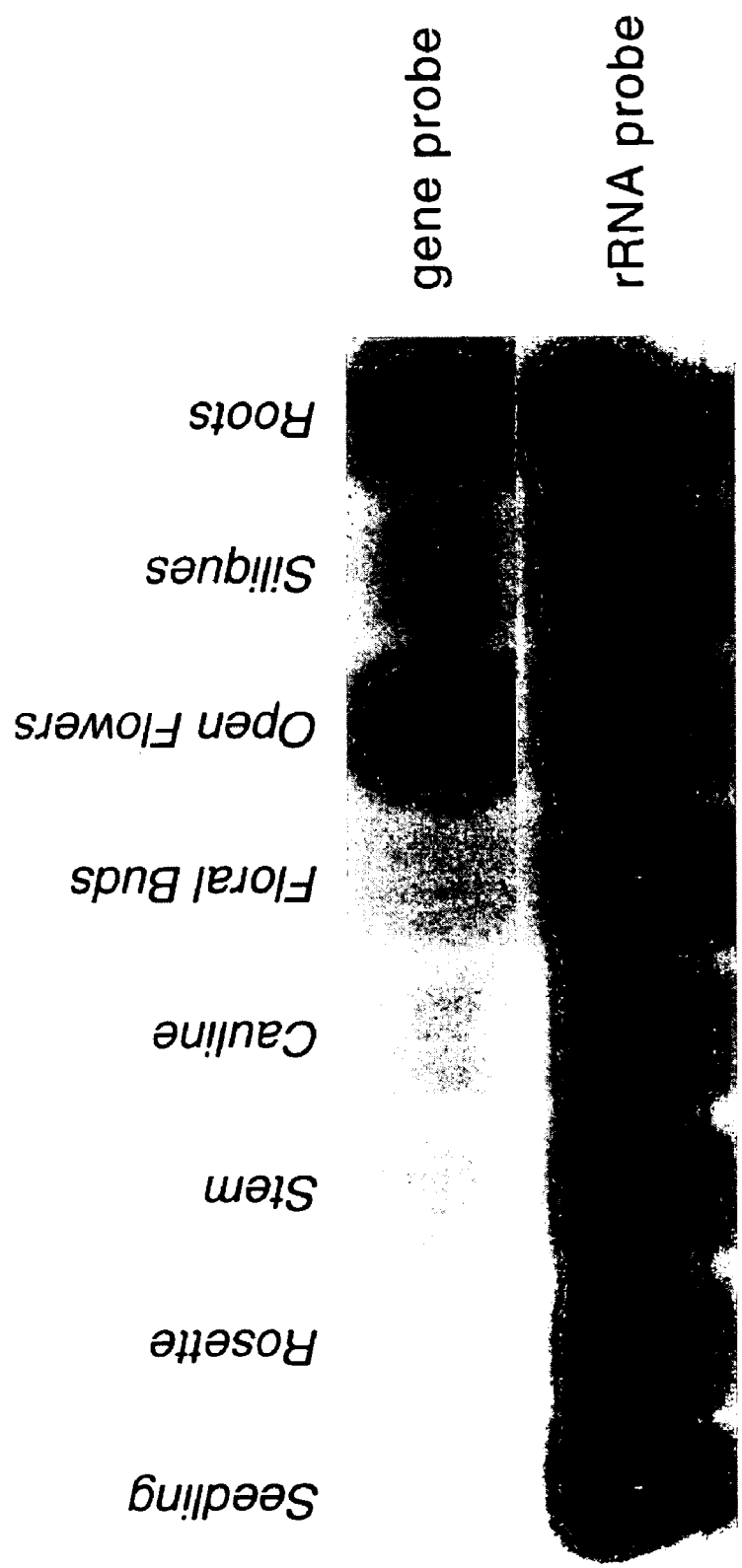
FIG. 1 is a photographic representation of a multi-tissue Northern blot analysis displaying the expression pattern of the plentiful gene in wild-type *Arabidopsis*. Total RNA (10) µg was electrophoresed and transferred to a nylon membrane before hybridizing to a $^{32}$P-labeled plentiful EST probe (gene probe). The membrane was then stripped and rehybridized to a ribosomal probe (rRNA probe).

The present invention is predicated in part on the identification of nucleic acid molecules capable of modifying the cellular matrix of a plant to produce plant cells and tissues which, upon regeneration, yield whole plants exhibiting altered characteristics and with desirable traits, and more particularly having tissues, organs or reproductive parts exhibiting altered architecture.

Accordingly, one aspect of the present invention contemplates a method for generating a plant with a modified plant phenotype, said method comprising introducing into the genome of one or more cells of a plant or one or more cells of a parent of said first-mentioned plant a nucleic acid molecule which, when expressed in cells of a plant, results in the phenotype of the cells being modified relative to cells not expressing said nucleic acid molecule.

Reference herein to a "plant" includes both monocotyledonous plants and dicotyledonous plants. Particularly useful plants are food crops such as wheat, rice, barley, soybean and sugar cane, and other non-food commercial crops such as cotton. Flower and ornamental crop plants, including, for example, rose, carnation, petunia, lisianthus, lily, iris, tulip, freesia, delphinium, limonium and pelargonium, are also encompassed within the scope of the invention. The instant invention further extends to forestry crops cultivated for wood-chips for pulp and paper production, or for timber production for the manufacture of wooden articles such as furniture. That is, all plants may fall within the scope of the present invention, including woody species. In accordance with this aspect of the present invention, a plant is first regenerated from the cell or cells into which the nucleic acid molecule has been introduced.

In a particularly preferred embodiment, the present invention contemplates a method for modulating plant tissue architecture, said method comprising introducing into the genome of one or more cells of a plant or one or more cells of a parent of said first-mentioned plant a nucleic acid molecule capable of effecting an alteration to cellular or tissue architecture and then regenerating a plant from said one or more cells.

Cellular and tissue architecture determine such phenotypic traits as size and shape of particular plant cells and tissues and hence of whole plantlets and adult plants. Modulation of a plant's cellular or tissue architecture may result in, for example, changes in cell shape to create larger more elongated structures, or to create smaller more compact structures; changes in cellular development leading to diversion of developmental pathways and concomitant absence of some tissues; changes in cell numbers leading to smaller or larger tissues, all of which changes ultimately lead to a modified phenotype such as, for example, shorter or longer stem tissue, reduced or increased lateral branching, preferential growth of inflorescence-bearing tissues rather than leaf-bearing tissues, decreased height and increased compactness of plant shape, to mention but a few.

The ability to control the modification of particular traits, singly or in concert, may provide the possibility to generate designer plants, exhibiting appropriate desired characteristics. Without wishing to limit the generality of the present invention, such modification of a plant's cellular or tissue architecture may be effected by modulation of a developmental or developmentally-regulated gene, leading to an alteration in the expression of one or more substrates or enzymes in a relevant biochemical pathway.

Accordingly, another aspect of the present invention is directed to a method for generating a plant with a modified phenotype, said method comprising introducing into the genome of one or more cells of said plant or one or more cells of a parent of said first-mentioned plant a nucleic acid molecule comprising a nucleotide sequence encoding or a sequence complementary to a nucleotide sequence encoding an amino acid sequence set forth in SEQ ID NO:2 or a derivative thereof including an amino acid sequence having at least about 75% sequence identity with SEQ ID NO:2 after optimal alignment and then regenerating a plant from said plant cells to produce a plant with said altered phenotype and optionally generating a progeny plant with said altered phenotype from said regenerated plant.

A related aspect of the present invention is directed to a method for facilitating the modification of a plant phenotype, said method comprising introducing into the genome of one or more cells of a said plant or one or more cells of a parent of said first-mentioned plant a nucleic acid molecule comprising a nucleotide sequence encoding or a sequence complementary to a nucleotide sequence encoding an amino acid sequence set forth in SEQ ID NO:2 or a derivative thereof including an amino acid sequence having at least about 75% identity to SEQ ID NO:2 after optimal alignment.

By "derivative" is meant a polypeptide that has been derived from the basic sequence by modification, for example, by conjugation or complexing with other chemical moieties or by post-translational modification techniques as would be understood in the art. The term "derivative" also includes within its scope alterations that have been made to a parent sequence including additions, or deletions that provide for functionally-equivalent molecules. Accordingly, the term "derivative" encompasses molecules that affect a plant's phenotype in the same way as does the parent an amino acid sequence from which it was generated. Also encompassed are polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

"Polypeptide", "peptide" and "an amino acid sequence" are used interchangeably herein to refer to a polymer of amino acid residues and to variants and synthetic analogues thereof. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers.

The term "derivative" also encompasses fragments. A "fragment", as used herein, means a portion or a part of a full-length parent polypeptide, which retains the activity of the parent polypeptide. As used herein, the term "biologically-active fragment" includes deletion mutants and small peptides, for example, of at least 10, preferably at least 20 and more preferably at least 30 contiguous amino acids, which comprise the above activity. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of an amino acid sequence of the invention with proteinases such as endoLys-C, endoArg-C, endoGlu-C and staphylococcus V8-protease. The digested fragments can be purified by, for example, high performance liquid chromatographic (HPLC) techniques. Any such fragment, irrespective of its means of generation, is to be understood to be encompassed by the term "derivative" as used herein.

In another aspect of the invention, there is provided a method for altering the phenotype of a plant, said method comprising introducing into the genome of one or more cells of said plant or one or more cells of a parent of said first-mentioned plant a nucleic acid molecule comprising a nucleotide sequence substantially as set forth in SEQ ID NO:1 or a variant or homolog thereof including a nucleotide sequence having at least about 75% sequence identity to SEQ ID NO:1 after optimal alignment or a nucleotide sequence capable of hybridizing to SEQ ID NO:1 or its complementary form under low stringency conditions.

The terms "variant" and "homolog" refer to nucleotide sequences displaying substantial sequence identity with a reference nucleotide sequences or polynucleotides that hybridize with a reference sequence under stringency conditions that are defined hereinafter. The terms "nucleotide sequence", "polynucleotide" and "nucleic acid molecule" may be used herein interchangeably and encompass polynucleotides in which one or more nucleotides have been added or deleted, or replaced with different nucleotides. In this regard, it is well understood in the art that certain alterations inclusive of mutations, additions, deletions and substitutions can be made to a reference nucleotide sequence whereby the altered polynucleotide retains the biological function or activity of the reference polynucleotide. The term "variant" also includes naturally-occurring allelic variants.

The extent of homology may be determined using sequence comparison programs such as GAP (Deveraux et al., 1984). In this way, sequences of a similar or substantially different length to those cited herein might be compared by insertion of gaps into the alignment, such gaps being determined, for example, by the comparison algorithm used by GAP, as is further discussed below.

Homologous sequences will generally hybridize under particular specified conditions. The term "hybridization" denotes the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

The extent of hybridization that may be displayed by homologous sequences depends on the conditions of, for example, temperature, ionic strength, presence or absence of certain organic solvents, under which hybridization and washing procedures are carried out. The higher the stringency, the higher will be the degree of complementarity between immobilised target nucleotide sequences and the labelled probe polynucleotide sequences that remain hybridized to the target after washing. "High stringency conditions" refers to temperature and ionic conditions under which only nucleotide sequences having a high frequency of complementary bases will hybridize. The stringency required is nucleotidesequence dependent, and further depends upon the various components present during hybridization and subsequent washes, and the time allowed for these processes. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences.

Reference herein to "low stringency conditions" is generally determined at 42° C. and includes and encompasses from at least about 0% v/v to at least about 15% v/v formamide, and from at least about 1 M to at least about 2 M salt for hybridization, and at least about 1 M to at least about 2 M for washing conditions. Alternative stringency conditions may be applied where necessary, such as: medium stringency, which includes and encompasses from at least about 16% v/v to at least about 30% v/v formamide, and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide, and from at least about 0.01 M to least about 0.15 M salt for hybridization, and at least about 0.01 M to at least about 0.15 M salt for washing conditions.

Suitably, the variant or homolog has at least about 75%, preferably at least about 80%, more preferably at least about 85%, more preferably at least about 90% and still more preferably at least about 95% sequence identity to the nucleotide sequence set forth in SEQ ID NO:1 or its complementary form. Variants and homologs may also correspond to derivatives of an amino acid sequence as set forth in SEQ ID NO:2. In one embodiment, derivatives have at least about 75%, preferably at least about 80%, more preferably at least about 85%, more preferably at least about 90% and still more preferably at least about 95% sequence identity to all or part of SEQ ID NO:2.

Terms used to describe sequence relationships between two or more nucleotide sequences or amino acid sequences include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al., 1997. A detailed discussion of sequence analysis can be found in Unit 19.3 of Ausubel et al., 1998.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e. the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

In accordance with the present invention, the nucleotide sequence set forth in SEQ ID NO:1 or a variant or homolog thereof or a nucleotide sequence capable of hybridizing to SEQ ID NO:1 or its complementary form under low stringency conditions or a nucleotide sequence having at least about 75% sequence identity with SEQ ID NO:1 or its complementary form after optimal alignment may be introduced into and optionally expressed in a recipient plant cell in order to create a desired phenotype. Phenotypes contemplated include but are not limited to increased lateral branching, more plentiful growth of inflorescence-bearing stems, and more plentiful inflorescences. A sequence complementary to the sequence set forth in SEQ ID NO:1 or a variant or homolog thereof or a sequence having at least about 75% sequence identity therewith may result in prevention of expression of the introduced sequence via any one of a number of processes known to those skilled in the art; for example, antisense suppression or sense suppression. Such down-regulation of gene expression may result in decreased lateral branching or increased growth of the primary shoot such as may be desired for the generation of trees suitable for the timber industry.

The term "expression" is used in its broadest sense and includes transient, semi-permanent and stable expression, as well as inducible, tissue-specific, constitutive and/or developmentally-regulated expression. Stable, tissue-specific expression is preferred.

Accordingly, introduction of the polynucleotide of SEQ ID NO:1 or a variant or homolog thereof or a nucleotide sequence capable of hybridizing to SEQ ID NO:1 or its complementary form under low stringency conditions or a nucleotide sequence having at least about 75% sequence identity with SEQ ID NO:1 or its complementary form after optimal alignment may result in modulated expression. The term "modulation" is used to emphasize that, although transcription may be increased or stabilised, this may have the effect of either permitting stabilized or enhanced translation of a product, or inducing transcript degradation such as via co-suppression, or post-transcriptional gene silencing.

To effect expression of the nucleotide sequence of the present invention, it may conveniently be incorporated into a chimeric genetic construct comprising inter alia one or more of the following: a promoter sequence, a 5' non-coding region, a cis-regulatory region such as a functional binding site for transcriptional regulatory protein or translational regulatory protein, an upstream activator sequence, an enhancer element, a silencer element, a TATA box motif, a CCAAT box motif, an upstream open reading frame, transcriptional start site, translational start site, and/or nucleotide sequence which encodes a leader sequence, and a 3' non-translated region. Preferable the chimeric genetic construct is designed for transformation of plants as hereinafter described.

The term "5' non-coding region" is used herein in its broadest context to include all nucleotide sequences which are derived from the upstream region of an expressible gene, other than those sequences which encode amino acid residues which comprise the polypeptide product of said gene, wherein 5' non-coding region confers or activates or otherwise facilitates, at least in part, expression of the gene.

The term "gene" is used in its broadest context to include both a genomic DNA region corresponding to the gene as well as a cDNA sequence corresponding to exons or a recombinant molecule engineered to encode a functional form of a product.

As used herein, the term "cis-acting sequence" or "cis-regulatory region" or similar term shall be taken to mean any sequence of nucleotides which is derived from an expressible genetic sequence wherein the expression of the first genetic sequence is regulated, at least in part, by said sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a structural gene or other nucleic acid molecule, in a plant cell. Preferred promoters according to the invention may contain additional copies of one or more specific regulatory elements to further enhance expression in a cell, and/or to alter the timing of expression of a structural gene to which it is operably connected.

The term "operably connected" or "operably linked" in the present context means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e. the genes from which it is derived.

Promoter sequences contemplated by the present invention may be native to the host plant to be transformed or may be derived from an alternative source, where the region is functional in the host plant. Other sources include the *Agrobacterium* T-DNA genes, such as the promoters for the biosynthesis of nopaline, octapine, mannopine, or other opine promoters; promoters from plants, such as the ubiquitin promoter; tissue specific promoters (see, e.g. U.S. Pat. No. 5,459,252; International Patent Publication No. WO 91/13992); promoters from viruses (including host specific viruses), or partially or wholly synthetic promoters. Numerous promoters that are functional in mono- and dicotyledonous plants are well known in the art (see, for example, Greve, 1983; Salomon et al., 1984; Garfinkel et al., 1983; Barker et al., 1983); including various promoters isolated from plants (such as the Ubi promoter from the maize ubi-1 gene, e.g. U.S. Pat. No. 4,962,028) and viruses (such as the cauliflower mosaic virus promoter, CaMV 35S).

The promoter sequences may include regions which regulate transcription, where the regulation involves, for example, chemical or physical repression or induction (e.g. regulation based on metabolites, light, or other physico-chemical factors; see, e.g. International Patent Publication No. WO 93/06710 disclosing a nematode responsive promoter) or regulation based on cell differentiation (such as associated with leaves, roots, seed, or the like in plants; see, e.g. U.S. Pat. No. 5,459,252 disclosing a root-specific promoter). Thus, the promoter region, or the regulatory portion of such region, is obtained from an appropriate gene that is so regulated. For example, the 1,5-ribulose biphosphate carboxylase gene is light-induced and may be used for transcriptional initiation. Other genes are known which are induced by stress, temperature, wounding, pathogen effects, etc.

The chimeric genetic construct of the present invention may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon.

The 3' non-translated regulatory DNA sequence preferably includes from about 50 to 1,000 nucleotide base pairs and may contain plant transcriptional and translational termination sequences in addition to a polyadenylation signal and any other regulatory signals capable of effecting mRNA processing or gene expression. Examples of suitable 3' non-translated sequences are the 3' transcribed non-translated regions containing a polyadenylation signal from the nopaline synthase (nos) gene of *Agrobacterium tumefaciens* (Bevan et al., 1983) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the pea E9 small sub-unit of the ribulose-1,5-bisphosphate carboxylase (ssRUBISCO) gene, although other 3' elements known to those of skill in the art can also be employed. Alternatively, 3' non-translated regulatory sequences can be obtained de novo as, for example, described by An (1987), which is incorporated herein by reference.

Accordingly, a further aspect of the present invention is directed to a method for altering the phenotype of a plant, said method comprising introducing into the genome of one or more cells of a plant or one or more cells of a parent of said first-mentioned plant a chimeric genetic construct comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

Even still another aspect of the present invention is directed to a vector in the form of a chimeric construct comprising a nucleic acid molecule having a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

Yet another aspect of the present invention provides a chimeric genetic construct comprising a nucleic acid molecule comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

A chimeric genetic construct can also be introduced into a vector, such as a plasmid. Plasmid vectors include additional DNA sequences that provide for easy selection, amplification, and transformation of the expression cassette in prokaryotic and eukaryotic cells, e.g. pUC-derived vectors, pSK-derived vectors, pGEM-derived vectors, pSP-derived vectors, or pBS-derived vectors. Additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the chimeric genetic construct, and sequences that enhance transformation of prokaryotic and eukaryotic cells.

The vector preferably contains an element(s) that permits either stable integration of the vector or a chimeric genetic construct contained therein into the host cell genome, or autonomous replication of the vector in the cell independent of the genome of the cell. The vector, or a construct contained therein, may be integrated into the host cell genome when introduced into a host cell. For integration, the vector may rely on a foreign or endogenous DNA sequence present therein or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector or a construct contained therein to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For cloning and sub-cloning purposes, the vector may further comprise an origin of replication enabling the vector to replicate autonomously in a host cell such as a bacterial cell. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. The origin of replication may be one having a mutation to make its function temperature-sensitive in a *Bacillus* cell (see, e.g. Ehrlich, 1978).

Accordingly, another aspect of the present invention contemplates a method for generating a plant with altered tissue architecture, said method comprising introducing into the genome of one or more cells of said plant or one or more cells of a parent of said first-mentioned plant a nucleic acid molecule comprising a nucleotide sequence encoding, or a sequence complementary to a nucleotide sequence encoding, an amino acid sequence set forth in SEQ ID NO:2 or a derivative thereof including an amino acid sequence having at least about 75% identity to SEQ ID NO:2 after optimal alignment and then regenerating a plant from said plant cells to produce a plant with said altered tissue architecture and optionally generating a progeny plant with said altered tissue architecture from said regenerated plant.

In a related aspect, there is contemplated a method for modifying plant tissue architecture, said method comprising introducing into the genome of one or more cells of said plant or one or more cells of a parent of said first-mentioned plant a nucleic acid molecule comprising a nucleotide sequence encoding, or a sequence complementary to a nucleotide sequence encoding, an amino acid sequence set forth in SEQ ID NO:2 or a derivative thereof including an amino acid sequence having at least about 75% identity to SEQ ID NO:2 after optimal alignment.

In work leading up to the present invention, the inventors sought to devise more efficacious methods for identifying the functions of the vast number of genetic sequences now available. In so doing, they developed binary vectors and chimeric genetic constructs to enable the rapid production of transgenic plants containing either sense or antisense copies of sequences of potentially-useful but unknown functions (Mylne and Botella, 1998).

In a most preferred embodiment, the chimeric genetic construct comprises the nucleotide sequence having the Genbank Accession Number T20918.

To facilitate identification of transformed cells, the vector desirably comprises a further genetic construct comprising a selectable or screenable marker gene. The actual choice of a marker is not crucial as long as it is functional (i.e. selective) in combination with the plant cells of choice. The marker gene and the nucleotide sequence of interest do not have to be linked, since co-transformation of unlinked genes as, for example, described in U.S. Pat. No. 4,399,216 is also an efficient process in plant transformation.

Included within the terms selectable or screenable marker genes are genes that encode a "secretable marker" whose secretion can be detected as a means of identifying or selecting for transformed cells. Examples include markers that encode a secretable antigen that can be identified by antibody interaction, or secretable enzymes that can be detected by their catalytic activity. Secretable proteins include, but are not restricted to, proteins that are inserted or trapped in the cell wall (e.g. proteins that include a leader sequence such as that found in the expression unit of extensin or tobacco PR-S); small, diffusible proteins detectable, for example, by ELISA; and small active enzymes detectable in extracellular solution such as, for example, α-amylase, β-lactamase, phosphinothricin acetyltransferase).

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (neo) gene conferring resistance to kanamycin, paromomycin, G418 and the like as, for example, described by Potrykus et al. (1985); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described International Patent Publication No. WO 87/05327, an acetyl transferase gene from *Streptomyces viridochromogenes* conferring resistance to the selective agent phosphinothricin as, for example, described in European Patent Application No. EP-A 275 957; a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in International Patent Publication No. WO 91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (European Patent Application No. EP-A-154 204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985), which may be employed in calcium-sensitive bioluminescence detection; a green fluorescent protein gene (Niedz et al., 1995); a luciferase (luc) gene (Ow et al., 1986), which allows for bioluminescence detection; a β-lactamase gene (Sutcliffe, 1978), which encodes an enzyme for which various chromogenic substrates are known (e.g. PADAC, a chromogenic cephalosporin); an R-locus gene, encoding a product that regulates the production of anthocyanin pigments (red colour) in plant tissues (Dellaporta et al., 1988); an α-amylase gene (Ikuta et al., 1990); a tyrosinase gene (Katz et al., 1983) which encodes an enzyme capable of oxidizing tyrosine to dopa and dopaquinone which in turn condenses to form the easily detectable compound melanin; or a xylE gene (Zukowsky et al., 1983), which encodes a catechol dioxygenase that can convert chromogenic catechols.

A further aspect of the present invention provides a transfected or transformed cell, tissue, or organ which comprises a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

The vectors and chimeric genetic construct(s) of the present invention may be introduced into a cell by various techniques known to those skilled in the art. The technique used may vary depending on the known successful techniques for that particular organism.

Techniques for introducing vectors, chimeric genetic constructs and the like into cells include, but are not limited to, transformation using $CaCl_2$ and variations thereof, direct DNA uptake into protoplasts, PEG-mediated uptake to protoplasts, microparticle bombardment, electroporation, microinjection of DNA, microparticle bombardment of tissue explants or cells, vacuum-infiltration of tissue with nucleic acid, and T-DNA-mediated transfer from *Agrobacterium* to the plant tissue.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 0.1 to 10 μm and more particularly 10.5 to 5 μm tungsten or gold spheres. The DNA construct may be deposited on the microparticle by any suitable technique, such as by precipitation.

Plant tissue capable of subsequent clonal propagation, whether by organogenesis or embryogenesis, may be transformed with a chimeric genetic construct of the present invention and a whole plant generated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g. apical meristem, axillary buds, and root meristems), and induced meristem tissue (e.g. cotyledon meristem and hypocotyl meristem).

The regenerated transformed plants may be propagated by a variety of means, such as by clonal propagation or classical breeding techniques. For example, a first generation (or T1) transformed plant may be selfed to give homozygous second generation (or T2) transformant, and the T2 plants further propagated through classical breeding techniques.

Accordingly, in another aspect of the present invention, there is provided a method for modifying plant tissue architecture, said method comprising introducing into the genome of one or more cells of said plant or one or more cells of a parent of said first-mentioned plant a nucleic acid molecule comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions.

In a related embodiment, the present invention provides a method for modifying plant tissue architecture, said method comprising introducing into the genome of one or more cells of said plant or one or more cells of a parent of said first-mentioned plant a vector comprising a chimeric genetic construct comprising a nucleotide sequence substantially as set forth in SEQ ID NO:1 or a variant or homolog thereof or a nucleotide sequence having at least about 75% identity to SEQ ID NO:1 after optimal alignment or a nucleotide sequence capable of hybridizing to SEQ ID NO:1 or its complementary form under low stringency conditions and then regenerating a plant from said plant cells to produce a plant with modified tissue architecture.

Accordingly, this aspect of the present invention, insofar as it relates to plants, further extends to progeny of the plants engineered to express a nucleotide sequence set forth in SEQ ID NO:1 or a variant or homolog thereof or a nucleotide sequence capable having at least about 75% identity to SEQ ID NO:1 after optimal alignment or a nucleotide sequence capable of hybridizing to SEQ ID NO:1 or its complementary form under low stringency conditions, as well as vegetative, propagative and reproductive parts of the plants, such as flowers (including cut or severed flowers), parts of plants, fibrous material from plants (for example, cotton) and reproductive portions including cuttings, pollen, seeds and callus.

Another aspect of the present invention provides a genetically modified plant cell or multicellular plant or progeny thereof or parts of said transgenic plant having an altered phenotype compared to its non-transformed equivalent, wherein said transgenic plant comprises the nucleotide sequence substantially as set forth in SEQ ID NO:1 or a variant or homolog thereof or a nucleotide sequence having at least about 75% identity to SEQ ID NO:1 or its complementary form under low stringency conditions.

More particularly, the present invention provides a genetically modified plant cell or multicellular plant or progeny or parts thereof comprising a nucleic acid molecule comprising a nucleotide sequence encoding or a sequence complementary to a nucleotide sequence encoding an amino acid sequence set forth in SEQ ID NO:2 or a derivative thereof or an amino acid sequence having at least about 75% identity to SEQ ID NO:2 after optimal alignment.

Even more particularly, the present invention provides a plant cell or multicellular plant or progeny thereof wherein said cell, plant, progeny or part thereof exhibits altered tissue architecture compared to its non-transformed equivalent.

The term "genetically modified" is used in its broadest sense and includes introducing gene(s) into cells, mutating gene(s) in cells and altering or modulating the regulation of gene(s) in cells. In the context of the present invention, a transgenic cell or plant line may also be considered as a mutant cell or plant line when compared with its non-transgenic counterpart.

Still another aspect of the present invention is directed to the use of a nucleic acid molecule comprising a nucleotide sequence substantially as set forth in SEQ ID NO:1 or a variant or homolog thereof including a nucleotide sequence having at least about 75% identity to SEQ ID NO:1 after optimal alignment or a nucleotide sequence capable of hybridizing to SEQ ID NO:1 or its complementary form under low stringency conditions in the manufacture of a transgenic plant having tissues with altered phenotype.

The present invention is further described by the following non-limiting Examples.

EXAMPLE 1

Preparation of Binary Vectors

An expression cassette for driving expression of chimeric constructs, which included a range of different ESTs of unknown functions, was generated by separately excising the CaMV35S promoter and the nos 3' terminator region from pBI121 (Bevan, 1984) and ligating them into the pUC18 multiple cloning site. This CaMV35S-polylinker-nos cassette was cloned into a binary vector backbone containing a Basta (registered trademark) resistance gene (bar) and a poly-linker (pSLJ75515, see Jones et al., 1992), which had previously had superfluous restriction enzyme sites removed. This binary vector was named, pAOV, and would become the backbone for the pSOV2 vector used to produce the plentiful phenotype (Mylne and Botella, 1998).

The multiple cloning site of pSOV2 was created by removing the cDNA clone insert of a PRL-2 clone (Newman et al., 1994) using SalI and NotI. The ends of the vector were blunt ended and the vector religated. The resulting plasmid (pZLD) is essentially pZL1 (D'Alessio et al., 1992) missing the restriction sites from SalI to NotI. The pZLD multiple cloning site was amplified by PCR using T7 and M13 primers and ligated into pAOV that had been previously modified to remove several conflicting restriction sites.

The pSOV2 binary vector was designed to allow the cloning of EST sequences from the *Arabidopsis* PRL-2 library in sense orientation. The purpose of this vector was the production of plants with extra copies of a particular gene to achieve either over-expression of the encoded protein or the overall down regulation of the gene by co-suppression events. EST sequences can be cloned using the PstI or EcoRI site at the 5' end of the EST clone and the XbaI, BamHI or HindIII sites at the 3' end. There are no spurious ATG codons in pSOV2 that could interfere with the start of translation of the encoded protein.

EST clones destined for pSOV2 were digested initially with BamHI and EcoRI and if any cut internally, they were digested with PstI, XbaI and HindIII until a suitable combination of enzymes was found that could achieve an asymmetric ligation. The plentiful EST was sub-cloned into pSOV2 using BamHI and EcoRI.

EXAMPLE 2

Transformation and Regeneration of *Arabidopsis*

A total of 89 EST clones were selected for use in binary vectors, 67 for the anti-sense strategy (destined for pAOV binary vector) and 22 for the sense over-expression strategy (destined for pSOV2 binary vector). Based on putative function, 77% of the ESTs for the anti-sense strategy (52) putatively belonged to the protein kinase family and the remaining 23% (15) were of unknown function. Sixty percent (13) of the full-length ESTs selected for the sense strategy were of unknown function. The remaining 9 were comprised of 6 putative protein kinases and 3 putative protein phosphatases.

Binary vectors were tri-parental mated into *Agrobacterium tumefaciens* (strain LBA4404) (Svab, Hajdukiewicz and Maliga, 1995) and the *Agrobacterium* suspension was used to transform adult *Arabidopsis* plants grown in soil pots (Bechtold, Ellis and Pelletier, 1993). Selection of transgenic plantlets was performed by sowing approximately 0.5 ml of seeds from infiltrated plants in soil trays (260 mm×310 mm). Germination was synchronized by treatment at 4° C. for 3-5 days. Trays were placed under long-day light at 21° C. and seedlings sprayed first upon emergence and twice afterwards at 3-day intervals with 0.4% Basta (registered trademark) (active constituent 20% glufosinate ammonium; Hoechst Schering Agrevo GmbH). Basta-resistant plants were transferred to pots and grown to maturity. Plants were observed during growth for the presence of altered phenotypes.

EXAMPLE 3

Identification of Expressed Sequence Tag (EST)

One particularly useful phenotype, designated plentiful, was found to have been generated upon introduction, in the sense direction, of the EST having Genbank Accession Number T20918. This EST had been derived from PRL-2 cDNA library (Newman et al., 1994, Plant Physiology 106(4): 1241), ordered from the *Arabidopsis* Information Management Service and supplied by the *Arabidopsis* Biological Resource Center (ABRC) at Ohio State University, U.S.A., as Clone_ID: 89I24T7. These plants were selected for further investigation.

EXAMPLE 4

Analysis of T2 *Arabidopsis* Plantlets

Co-Segregation of the Phenotype with Basta (Registered Trademark) Resistance

To prove that the transgene was responsible for the phenotype, $T_2$ seed was sown on soil and at three weeks, leaves of all $T_2$ plants were painted with 0.08% Basta (registered trademark) (active constituent 20% glufosinate ammonium) and scored for their response to Basta two days later. The results of this analysis are presented in Table 1, below:

TABLE 1

Co-segregation of the plentiful phenotype with the Basta (registered trademark) transgene

| | Basta Resistant | | Basta Sensitive | | | |
|---|---|---|---|---|---|---|
| Line | Mutant | Wild | Mutant | Wild | Co-seg | Ratio R:S |
| 116-04 | 79 | 0 | 0 | 16 | 100% | 4.4:1 |
| 116-05 | 115 | 0 | 0 | 8 | 100% | 15:1 |

EXAMPLE 5

Northern Analyses

Figure 2:
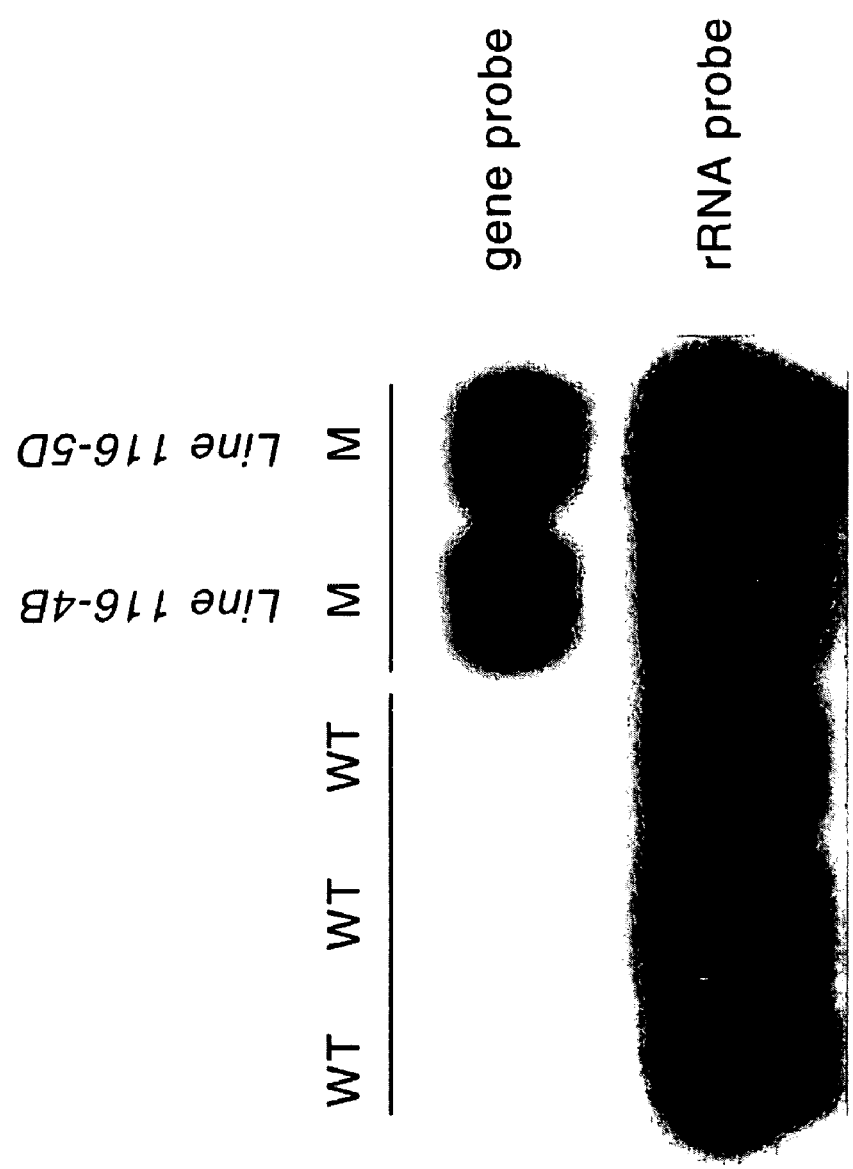
FIG. 2 is a photographic representation of Northern analysis of two independent plentiful transgenic lines and three separate wild-type samples. Total RNA (10 µg) from 2-week seedlings was electrophoresed and transferred to a nylon membrane before hybridizing to a $^{32}$P-labeled plentiful EST probe (gene probe). The membrane was then stripped and rehybridized to a ribosomal probe (rRNA probe).
Figure 3:
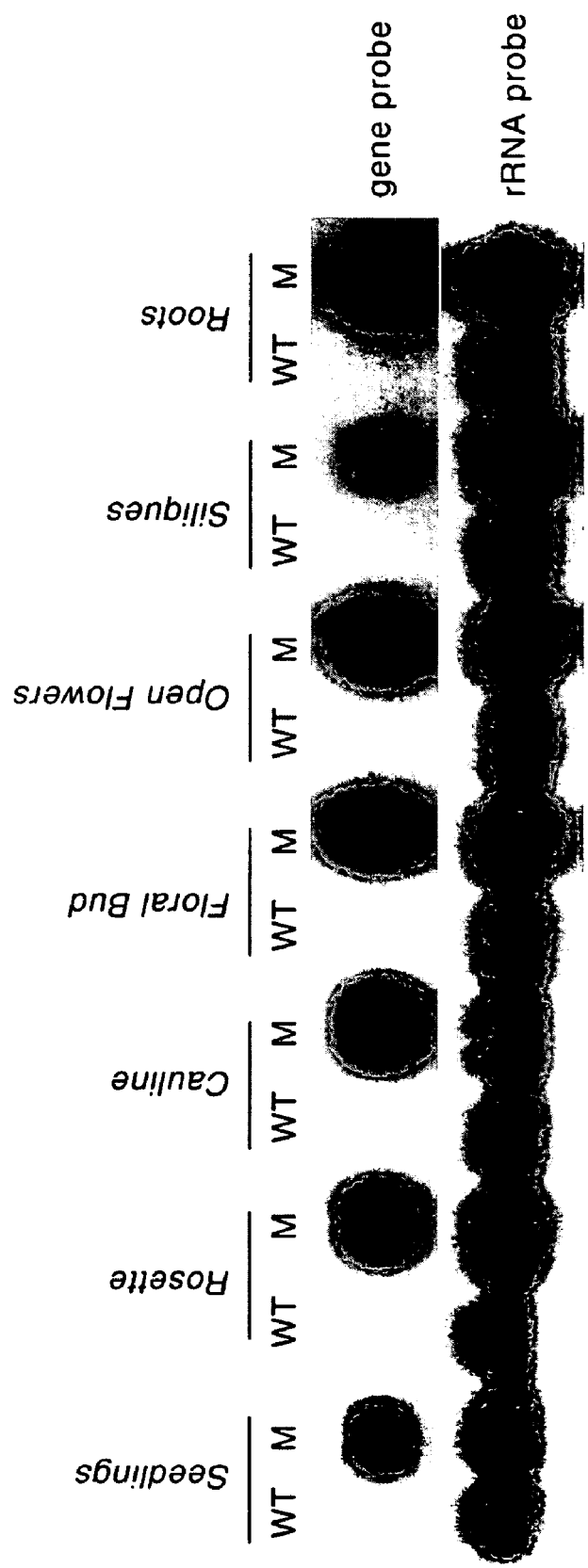
FIG. 3 is a photographic representation of Northern analysis of different tissues of the transformed plentiful line 116-5D (M) and wild-type phenotype non-transformed segregant lines (WT). Total RNA (10 µg) was electrophoresed and transferred to a nylon membrane before hybridizing to a $^{32}$P-labeled plentiful EST probe (gene probe). The membrane was then stripped and rehybridized to a ribosomal probe (rRNA probe).

RNA for the multi-tissue Northern and transgenic Northern of seedling tissue (FIGS. 1 and 2) was extracted as by (Etheridge et al., 1999). The LiCl supernatant from this method contained the genomic DNA used for the Southern blot analysis (FIG. 4). RNA for the multi-tissue transgenic Northern (FIG. 3) was prepared by the following method. Small amounts of frozen tissue were ground into a fine powder and vortexed for 1 min in a mixture of 0.5 ml of 100 mM Tris-HCl (pH 8.0) containing 100 mM NaCl, 5 mM EDTA, 0.5% w/v SDS and 0.5 ml of phenol/chloroform/isoamyl alcohol (25:24:1). This mixture was centrifuged and 400 μl of the aqueous phase added to 800 μl of ethanol to precipitate the nucleic acids. After centrifugation for 5 min, the total nucleic acid pellet was dried and resuspended in 50 μl of water.

RNA was fractionated on a 1% w/v agarose (0.5×TBE) gel and transferred to a nylon membrane by capillary blotting and probing with $^{32}$P-labeled fragment using standard laboratory techniques (Sambrook et al., 1989).

(a) Northern analysis of wild-type gene expression showed that plentiful gene expression was highest in open flowers and roots (refer to FIG. 1). This suggested that the phenotype must be caused by expression of this tissue-specific message, throughout all tissues, at greatly elevated levels.

(b) To prove that the CaMV35S promoter was driving over-expression of the plentiful transcript, total RNA was extracted from 3 wild-type lines and two independent transgenic plentiful lines (lines 4B and 5D) and examined by Northern analysis. The autoradiography clearly showed that there was over-expression of the plentiful transcript in both independent transgenic lines.

(c) To prove that the CaMV35S promoter was driving constitutive over-expression of the plentiful transcript, total RNA was extracted from different tissues of wild-type and plentiful line 5D. The autoradiograph of the Northern blot, probed with the plentiful gene fragment clearly shows the over-expression of the tran script in all the plentiful tissues tested. Wild-type expression is not visible as expected, considering the low expression levels of the plentiful transcript. By contrast, the CaMV35S-driven over-expression in the plentiful line is easily detectable.

EXAMPLE 6

Southern Analyses of Independent Transformation Events

To demonstrate that the phenotype did not arise from an insertion event (independent transformation), 3 μg of genomic DNA from wild-type plants and two lines displaying the plentiful phenotype was digested with one of EcoRI, HindIII and SalI. The digested DNA was electrophoresed and transferred to a nylon membrane. The membrane was probed with $^{32}$P-labeled 35S probe (see FIG. 4A). The Southern blot probed with the 35S promoter shows that lines 116-4B and 116-5D contain both single insertions of the T-DNA. As expected, no hybridization of the 35S probed was detected in wild-type (WT) DNA. This Southern blot clearly shows that these two transgenics lines arise from independent transformation events.

Figures 4A, 4B:
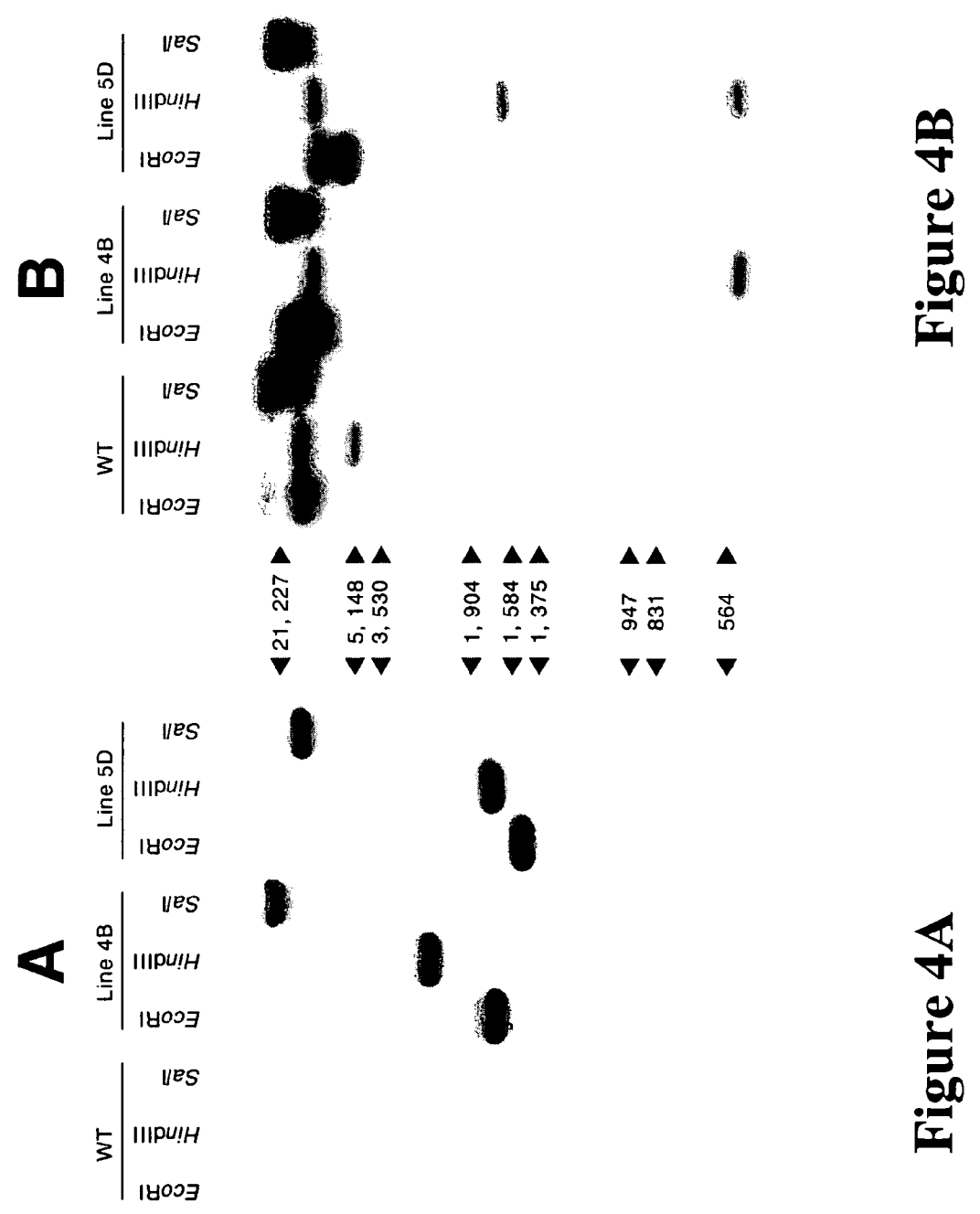
Figure 5:
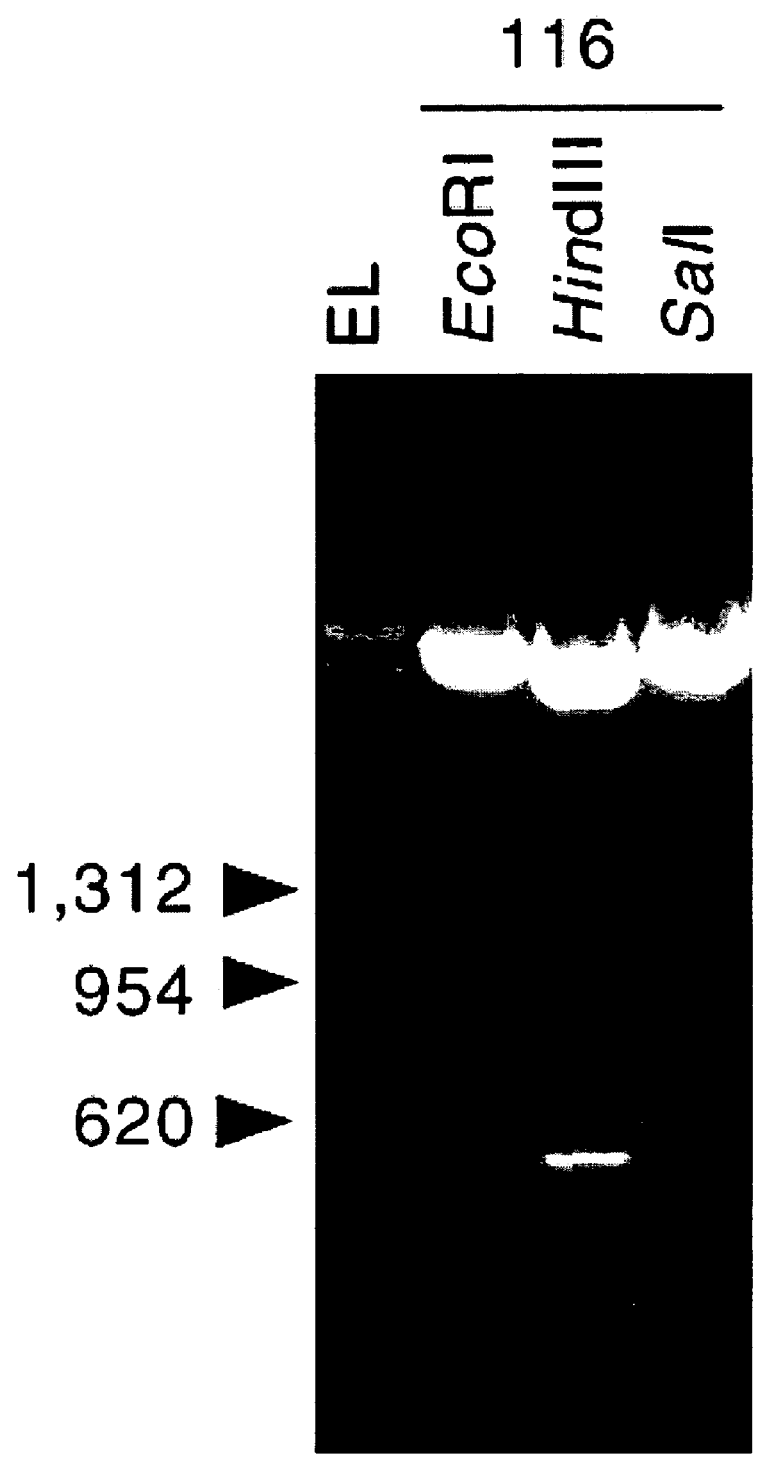
FIG. 5 is a photographic representation of Southern analysis, showing a restriction digest of the plentiful EST in the PRL-2 library plasmid, pZL1. Plasmid DNA (1 µg) was digested separately with EcoRI, HindIII and SalI, the same enzymes used in the Southern blot shown in FIG. 4, and electrophoresed on a 0.8% v/v agarose gel. Size markers are also indicated. Refer to Example 6 for further discussion.
Figure 6:
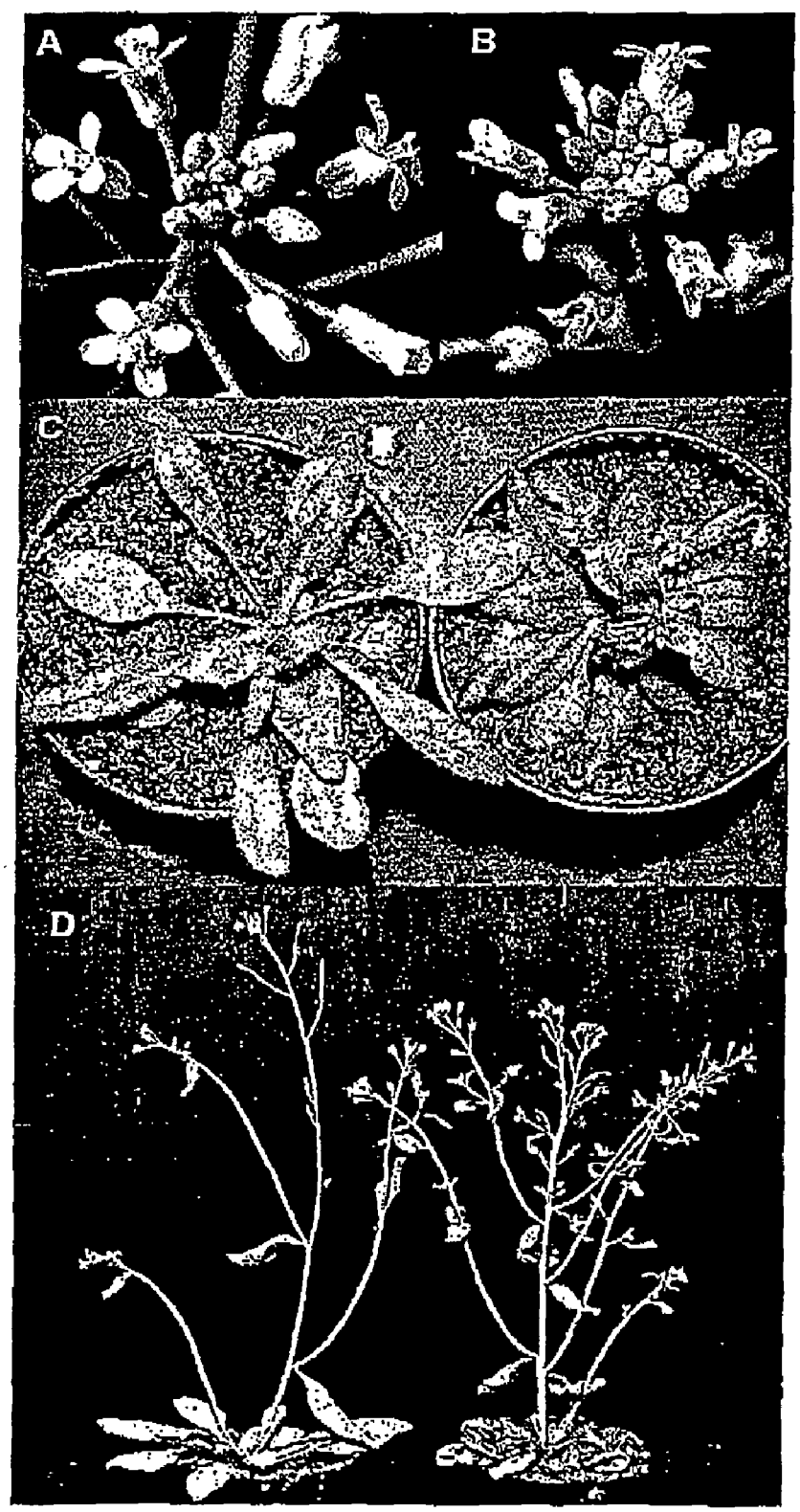
FIGS. 6A-D are photographic representations showing the different phenotypes of wild-type *Arabidopsis* (Columbia) plants, compared to the plentiful phenotypes of the transformed plants of the present invention: FIG. A shows wild-type inflorescence; FIG. B shows plentiful phenotype inflorescence head; FIG. C shows non-transformed 25-day-old segregant on the left of the picture, and 49-day-old plentiful phenotype on the right of the picture, at similar developmental stages; and FIG. D shows wild-type 31-day-old phenotype on the left, and 64-day-old plentiful phenotype on the right of the picture.

The membrane was then stripped and rehybridized to a plentiful EST probe (see FIG. 4B). The Southern blot probed with the plentiful EST probe should detect both the wild-type copy of the gene and the additional copy of the plentiful gene included in the transferred T-DNA. Digestion of the plentiful EST clone with EcoRI, HindIII and SalI shows that it contains and internal HindIII site (FIG. 5). HindIII cuts once inside the gene sequence and once in the polylinker of pZL1, outside the 3' end of the gene. When transferred to pSOV2, the HindIII site of pSOV2 will produce the same 500 bp band upon digestion of the pSOV2-116 sense construct. The HindIII lanes of the Southern blot show DNA from both transgenics liberate a 500 bp homologous to the plentiful EST probe.

Combined, these Southern blots confirm that the plentiful transgenics contain the correct T-DNA region of the pSOV2-116 binary construct and that the phenotype did not arise from an insertion event.

EXAMPLE 7

Description of Resulting Phenotype

The selected plants exhibited a number of characteristic upon which they could be distinguished from their non-transgenic equivalents, including: altered aerial architecture, alterations in leaf number and morphology, and increase in the thickness of organs, alteration in silique numbers and morphology and a delay in development.

Aerial Architecture

There was a significant difference between the general architecture of wild-type and that of plentiful phenotype. This difference was consistent throughout the plant in primary bolts, primary lateral branches, secondary lateral branches and secondary bolts produced. Plants displaying the plentiful phenotype were generally smaller and more compact resembling a wild-type plant that had been compressed. Bolts and lateral branches were shorter and branches were placed closer together (smaller internodal distance). Branches were positioned closer to the base of the bolt (or branch in the case of secondary branches) and a larger number of secondary lateral branches were produced. Similarly, the first silique in plentiful plants was closer to the base of the bolt (or branch). All these features gave plentiful plants a bushy appearance.

Both wild-type and plentiful plants produced roughly the same number of primary lateral branches. However, differences emerge when secondary lateral branches are examined. 'Plentiful' plants consistently produced a larger number of cauline leaves and secondary lateral branches than the wild-type. 'Plentiful' plants tended to extend secondary lateral branch primordia generally from later cauline leaf positions whereas the wild-type tended to extend primordia earlier.

TABLE 2

Comparison of general bolt and branch architecture of 'Plentiful' plants and non-transformed segregants (NTS)

|  | NTS | 116-5D |
| --- | --- | --- |
| Primary bolt height (mm ± standard error) | 347.67 ± 0.09 | 238.47 ± 2.91 |
| Average number of primary lateral branches | 3.60 ± 0.11 | 3.59 ± 0.13 |
| Average number of secondary lateral branches | 4.23 ± 0.36 | 5.59 ± 0.38 |

Leaves

The rosette leaves of the plentiful plant differed significantly from the wild-type in all three characteristics examined (see Table 3). The most noticeable difference was leaf length, where plentiful averages 8 mm shorter than wild-type. This decrease when coupled with an increase in leaf width produced rosette leaves that were rounder, almost square, compared with wild-type rosette leaves that had typical elongated oval shapes. 'Plentiful' rosette leaves had a shorter petiole length and the connection between the rosette leaf and petiole was less tapered. 'Plentiful' also produced a larger number of rosette leaves. Together, these alterations created a rosette that was smaller and more compact than the wild-type. In addition to showing a dark green colour, the rosette leaves were more rigid than the wild-type perhaps due to an increase in leaf thickness or compactness.

TABLE 3

Comparison of rosette leaf dimensions of plentiful and non-transformed segregants (NTS) (average mm ± std. deviation, n = 29)

|  | NTS | 116-5D |
| --- | --- | --- |
| Petiole Length | 9.71 ± 0.51 | 7.00 ± 0.54 |
| Leaf Length | 26.09 ± 2.06 | 18.19 ± 0.99 |
| Leaf Width | 14.87 ± 0.81 | 18.28 ± 0.91 |

Organ Thickness

'Plentiful' plants have thicker organs than wild-type plants. Measurements suggest an average increase of 16.5% in organ thickness for plentiful plants.

TABLE 4

Organ thickness of wild-type and plentiful plants (Line 116-5D) in average mm ± standard error

|  | NTS | 116-5D | % Increase |
|---|---|---|---|
| Primary Bolt | 1.20 ± 0.04 | 1.32 ± 0.02 | 9.5 |
| Lateral Branch 1 | 0.97 ± 0.04 | 1.04 ± 0.02 | 7.5 |
| Lateral Branch 2 | 0.87 ± 0.03 | 1.10 ± 0.10 | 27.0 |
| Lateral Branch 3 | 0.80 ± 0.04 | 0.92 ± 0.03 | 16.3 |
| Lateral Branch 4 | 0.77 ± 0.06 | 0.92 ± 0.06 | 19.5 |
| Silique | 0.58 ± 0.03 | 0.69 ± 0.02 | 19.3 |

Siliques

The inflorescence meristem of plentiful produced siliques that did not move from the inflorescence apex as quickly as the wild-type. The siliques were more closely spaced, had a shorter petiole and were shorter than the wild-type. These characteristics gave inflorescences a 'bristly' appearance. The siliques of both wild-type and plentiful plants held a variable number of seeds and were not significantly different (58.31±3.33 and 58.33±1.16 respectively). 'Plentiful' siliques were fatter and had a bumpier surface compared to wild-type siliques. The phyllotactic angles of siliques of NTS and plentiful plants were significantly different with an angle of 148.960° (degrees)±1.80 and 131.42±1.93, respectively. Plentiful plants produced more siliques than the wild-type in all locations studied and by total silique number (233±5.69 for plentiful vs. 211±9.36 for wild-type) The distribution of siliques on plentiful plants was similar to that of the wild-type.

TABLE 5

Silique measurements on different parts of wild-type and plentiful Arabidopsis (line 116-5D). Values are average mm ± standard error.

|  | Bolt | | Primary Lateral Branch | | Secondary Bolt | |
|---|---|---|---|---|---|---|
|  | NTS | 116-5D | NTS | 116-5D | NTS | 116-5D |
| Silique petiole length | 7.95 ± 0.19 | 5.53 ± 0.15 | 6.50 ± 0.10 | 5.46 ± 0.10 | 6.00 ± 0.12 | 4.18 ± 0.21 |
| Silique length | 14.26 ± 0.68 | 10.16 ± 0.19 | 13.53 ± 0.35 | 10.12 ± 0.13 | 12.39 ± 0.43 | 9.03 ± 0.17 |
| Inter-silique distance | 10.02 ± 0.80 | 6.48 ± 0.50 | 7.42 ± 0.52 | 5.94 ± 0.47 | 7.01 ± 0.76 | 4.79 ± 0.79 |

Developmental Timing

Plentiful has a longer vegetative stage showing an approximate delay of 11 days for the transition to flowering. However, after bolting, the inflorescence meristem in plentiful and NTS plants develop at the same speed (i.e. if plentiful plants were planted 11 days before NTS, no difference would be observed in table below). The plentiful plants also have a significant difference in the time to senesce. Senescence was attributed to plants when the first seed pod lost its green pigmentation and turned yellow. The outcome of this measurement was supported by images of the rosette of wild-type and plentiful plants at 50 days. The rosette of the plentiful plant is still green while most of the rosette of the wild-type plant has lost pigmentation and is clearly in the mid to late stages of senescence (see FIG. 7).

Figure 7:
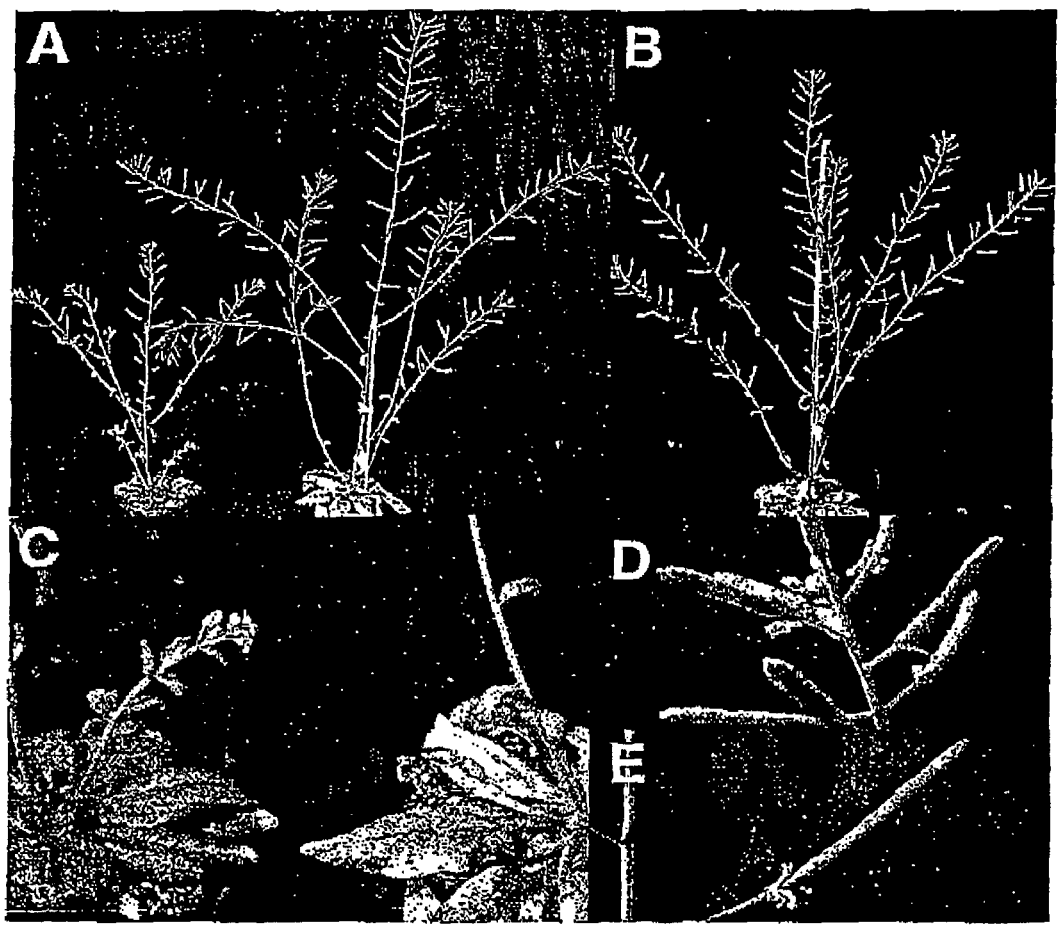
FIGS. 7A-E are photographic representations showing mature plentiful phenotypes and wild-type *Arabidopsis*. FIG. A shows Plentiful phenotype (left) and wild-type *Arabidopsis* plants at 50 days; FIG. B shows Plentiful phenotype 11 days later at end of reproductive phase; FIG. C shows close up image of rosette leaves of plentiful phenotype (left) and wild-type *Arabidopsis* (right) at 50 days; white arrows indicate regions of severe senescence; FIG. D shows close up of siliques of plentiful phenotype; and FIG. E shows close up of siliques of wild-type phenotype.

FIG. 7 shows the difference in the stage of development at 50 days for adult plentiful plants and wild-type *Arabidopsis* plants. Plentiful is still in the middle of the reproductive (flowering) phase while the wild-type *Arabidopsis* at the same stage has completed flowering. The close up of the rosettes of the whole plants in (A) above shows that the wild-type rosette leaves are in an advanced stage of senescence. The white arrows pointing to dead leaves and chlorotic (yellowing) tissue. The loss of pigmentation in the wild-type plant (change from green to yellow) is difficult to visualize using a gray-scale colour scheme. The abnormal 'bumps' in plentiful seed pods are shown compared to the smooth exterior of a wild-type *Arabidopsis*.

TABLE 6

Development of wild-type and Plentiful (Line 116-5D) in average days ± standard error

|  | NTS | 116-5D | Delay |
|---|---|---|---|
| Days to bolting (4 cm bolt) | 36.76 ± 0.22 | 47.30 ± 0.33 | 11 days |
| Days to 1st lateral branch | 36.66 ± 0.17 | 44.91 ± 0.29 | 8 days |
| Days to 1st secondary bolt | 38.55 ± 0.30 | 47.05 ± 0.32 | 9 days |
| Days to 1st flower | 37.00 ± 0.31 | 46.22 ± 0.47 | 9 days |
| Days to 20th flower | 44.46 ± 0.63 | 52.39 ± 0.33 | 8 days |
| Days to senescence (1st yellow silique) | 51.95 ± 0.33 | 60.97 ± 0.44 | 9 days |

EXAMPLE 8

Identity of Genetic Sequence Encoding the Plentiful Phenotype

The sequence for the plentiful phenotype (SEQ ID NO:1), in GCG format, is as shown below. Base-pairs of the sequence are numbered on the left-hand side. Base-pairs 1-84=5' untranslated region; 85-87=start ATG (bold); base-pairs 85-389=protein coding region; 391-393=stop TAA (bold); base-pairs 394-614=3' untranslated region.

[SEQ ID NO:1]

ATACTCTCAT ATATATTTGC ATCTAATCTT GTAAGCAAAC

GTTATCACTT GTCTACACAA CATTCTTTCA TTTACAATAA

TAATATGGGT GTAACATTAG AAGGACAAAG AAAGGAATCA

ATTTGGGTTT TGATGAGAAG ACAAAGGGCT CGAAGGGCAC

TTGTGAAGAA GATCATGATC CGACCAAGGA AGAGTGTAGA

AGCTTCTAGA AGACCTTGTC GCGCAATACA CAGACGAGTG

```
                    -continued
AAGACGCTAA AAGAGCTTGT TCCCAACACC AAAACATCAG

AAGGTTTAGA TGGACTCTTT AGACAAACGG CAGATTATAT

CTTGGCTTTG GAAATGAAAG TGAAAGTTAT GCAGACAATG

GTTCAGGTTT TGACCGAAAC TAACTGTGTT TAAAAGCCTT

CATATATTTT TTGTATATCT TGTTGGATTT TACGTTCTTT

TTAGTTTTTA TTTGTTCGTG TTTATTTTTT ATTATCTCGT

GTGATTGTCT TGTGTTGCTT ATATAGAAAA GGAATTTGGT

TTATCTTGCT GCTGTAGACT ATGCAGAAAA TTAAATATCA

AAAATATATA TGTATTATAT GCTTATCTAA ATAACAGATG

ACTGTTGGTT CGGC
```

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

Altschul et al. (1997) Nucl. Acids Res. 25: 3389.
An (1987) Methods of Enzymology 153: 292.
Ausubel et al., "Current Protocols in Molecular Biology" John Wiley & Sons Inc, 1994-1998, Chapter 15.
Barker et al. (1983) Plant Mol. Biol. 2: 235-350.
Bechtold, N., Ellis, J. & Pelletier, G. (1993). In planta Agrobacterium mediated gene transfer by infiltration of adult Arabidopsis thaliana plants. Comptes Rendus de l'Academie des Sciences Serie III Sciences de la Vie 316: 1194-1199.
Bevan et al. (1983) Nucl. Acid. Res. 11: 369.
Bevan, M. (1984). Binary Agrobacterium vectors for plant transformation. Nucleic Acids Research 12: 8711-8721.
Bonner and Laskey, (1974) Eur. J. Biochem. 46: 83.
D'Alessio, J. M., Bebee, R., Hartley, J. L., Noon, M. C. & Polayes, D. (1992). Lambda Ziplox: Automatic Subcloning of cDNA. Focus 14; 76-79.
Dellaporta et al. (1988) in Chromosome Structure and Function pp. 263-282.
Ehrlich (1978) Proc. Natl. Acad. Sci. USA 75: 1433.
Etheridge, N., Trusov, Y., Verbelen, J. P. & Botella, J. R. (1999). Characterization of ATDRG1, a member of a new class of GTP-binding proteins in plants. Plant Molecular Biology 39: 1113-1126.
Garfinkel et al. (1983) Cell 27: 143-153.
Greve, 1983, J. Mol. Appl GEnet. 1: 499-511.
Hinchee et al. (1988) Biotech 6: 915.
Ikuta et al. (1990) Biotech 8: 241.
Jones, J. D., Shlumukov, L., Carland, F., English, J., Scofield, S. R., Bishop, G. J. & Harrison, K. (1992). Effective vectors for transformation, expression of heterologous genes, and assaying transposon excision in transgenic plants. Transgenic Research 1; 285-297.
Katz et al. (1983) J. Gen. Microbiol. 129: 2703.
Marmur and Doty (1962) J. Mol. Biol. 5: 109.
Mylne, J. S. & Botella, J. R. (1998). Binary vectors for sense and antisense expression of Arabidopsis ESTs. Plant Molecular Biology Reporter 16: 257-262.
Newman, T., De-Bruijn, F. J., Green, P., Keegstra, K., Kende, H., McIntosh, L., Ohlrogge, J., Raikhel, N., Somerville, S., Thomashow, M., Retzel, E. & Somerville, C. (1994). Genes Galore: A Summary of Methods for Accessing Results from Large-Scale Partial Sequencing of Anonymous Arabidopsis cDNA Clones. Plant Physiology 106: 1241-1255.
Niedz et al. (1995) Plant Cell Reports 14: 403.
Ow et al. (1986) Science 234: 856.
Potrykus et al. (1985) Mol. Gene. Genet. 199: 183.
Prasher et al. (1985) Biochem. Biophys. Res. Comm. 126: 1259.
Salomon et al. (1984) EMBO J. 3: 141-146.
Sambrook, J., Fritsch, E. F. & Maniatis, T. (1989). Molecular Cloning: a Laboratory Manual, 2nd edition. Cold Spring Harbor Laboratory Press, New York.
Sutcliffe (1978) Proc. Natl. Acad. Sci. USA 75: 3737.
Svab, Z., Hajdukiewicz, P. & Maliga, P. (1995). Generation of transgenic tobacco plants by cocultivation of leaf disks with Agrobacterium pPZP binary vectors. In Methods in plant molecular biology: a laboratory course manual. A Cold Spring Harbor Laboratory course manual (ed. P. Maliga, D. F. Klessig, A. R. Cashmore, W. Gruissem and J. E. Varner), pp. 55-77. Cold Spring Harbor Laboratory Press, Plainview, N.Y.
Thillet et al. (1988) J Biol. Chem. 263: 12500.
Zukowsky et al. (1983) Proc. Natl. Acad. Sci. USA 80: 1101.

What is claimed is:

1. A method for generating a plant with a modified plant phenotype comprising introducing into the genome of one or more cells of said plant a nucleic acid molecule comprising a nucleotide sequence encoding the amino acid sequence set forth in SEQ ID NO:2 or the complement thereof, and then regenerating a plant from said plant cells to produce a plant with said modified phenotype and optionally generating a progeny plant with said modified phenotype from said regenerated plant, wherein said progeny plant comprises the nucleic acid molecule and wherein said modified phenotype is selected from the group consisting of: smaller and more compact stature, shorter bolt and lateral branches, smaller internodal distance, branches positioned closer to the base of the plant, more lateral branches, more cauline leaves, leaves are shorter and wider, more rosette leaves, thicker leaves, more siliques, and a longer vegetative stage compared to a control plant.

2. The method of claim 1, wherein the plant having a modified phenotype is the regenerated plant.

3. The method of claim 1, wherein the plant having a modified phenotype is a progeny of said regenerated plant and wherein said progeny plant comprises said nucleic acid molecule.

4. A method for facilitating the modification of a plant phenotype comprising introducing into the genome of one or more cells of said plant a nucleic acid molecule comprising a nucleotide sequence encoding the amino acid sequence set forth in SEQ ID NO:2 or the complement thereof and wherein said phenotype is selected from the group consisting of: smaller and more compact stature, shorter bolt and lateral branches, smaller internodal distance, branches positioned closer to the base of the plant, more lateral branches, more cauline leaves, leaves are shorter and wider, more rosette leaves, thicker leaves, more siliques, and a longer vegetative stage compared to a control plant.

5. The method of claim 4, further comprising regenerating a plant from the one or more cell of said plant, wherein the progeny of the regenerated plant has a modified phenotype and wherein said progeny comprises said nucleic acid molecule.

6. A method for altering the phenotype of a plant, said method comprising introducing into the genome of one or more cells of said plant a nucleic acid molecule comprising a nucleotide sequence as set forth in SEQ ID NO:1, or the complement thereof wherein said altered phenotype is selected from the group consisting of: smaller and more compact stature, shorter bolt and lateral branches, smaller internodal distance, branches positioned closer to the base of the plant, more lateral branches, more cauline leaves, leaves are shorter and wider, more rosette leaves, thicker leaves, more siliques, and a longer vegetative stage compared to a control plant.

7. The method of claim 6, wherein the nucleic acid molecule is comprised in a chimeric genetic construct.

8. The method of claim 7, wherein the chimeric genetic construct is comprised in a vector.

9. A method for generating a plant with altered tissue architecture, said method comprising introducing into the genome of one or more cells of said plant a nucleic acid molecule comprising a nucleotide sequence encoding the amino acid sequence set forth in SEQ ID NO:2, or the complement thereof, and then regenerating a plant from said plant cells to produce a plant with said altered tissue architecture and optionally generating a progeny plant with said altered tissue architecture from said regenerated plant, wherein said progeny plant comprises the nucleic acid molecule and wherein said altered tissue architecture is selected from the group consisting of: changes in cell shape, changes in cellular development and changes in cell numbers.

10. The method of claim 9, wherein the plant having altered tissue architecture is a regenerated plant.

11. The method of claim 9, wherein the plant having altered tissue architecture is a progeny of said regenerated plant and wherein said progeny plant comprises said nucleic acid molecule.

12. A method for modifying plant tissue architecture, said method comprising introducing into the genome of one or more cells of said plant a nucleic acid molecule comprising a nucleotide sequence encoding the amino acid sequence set forth in SEQ ID NO:2 or the complement thereof wherein said modifying tissue architecture is selected from the group consisting of: changes in cell shape, changes in cellular development and changes in cell numbers.

13. The method of claim 12, further comprising regenerating a plant from the plant cells having the introduced nucleotide sequence, wherein a progeny of the regenerated parent plant has modified tissue architecture and comprises the introduced nucleic acid molecule.

14. A method for modifying plant tissue architecture, said method comprising introducing into the genome of one or more cells of said plant a nucleic acid molecule comprising a nucleotide sequence as set forth in SEQ ID NO:1, or the complement thereof and wherein said modifying tissue architecture is selected from the group consisting of: changes in cell shape, changes in cellular development and changes in cell numbers.

15. The method according to claim 1, wherein the plant is a monocotyledonous plant.

16. The method according to claim 1, wherein the plant is a dicotyledonous plant.

17. A genetically modified plant cell, plant, progeny thereof or parts of said genetically modified plant, generated in accordance with the method of claim 1 which comprises a nucleotide sequence as set forth in SEQ ID NO:1, or the complement thereof.

18. A genetically modified plant cell, plant, progeny or parts thereof generated in accordance with the method of claim 1, comprising a nucleic acid molecule comprising a nucleotide sequence encoding the amino acid sequence set forth in SEQ ID NO:2 or the complement thereof.

19. The plant cell, plant, progeny or parts thereof of claim 17, wherein said cell, plant, progeny or part thereof exhibits altered tissue architecture compared to its non-transformed equivalent wherein said altered tissue architecture is selected from the group consisting of: changes in cell shape, changes in cellular development and changes in cell numbers.

20. The method according to claim 4, wherein the plant is a monocotyledonous plant.

21. The method according to claim 6, wherein the plant is a monocotyledonous plant.

22. The method according to claim 9, wherein the plant is a monocotyledonous plant.

23. The method according to claim 12, wherein the plant is a monocotyledonous plant.

24. The method according to claim 12, wherein the plant is a monocotyledonous plant.

25. The method according to claim 4, wherein the plant is a dicotyledonous plant.

26. The method according to claim 6, wherein the plant is a dicotyledonous plant.

27. The method according to claim 9, wherein the plant is a dicotyledonous plant.

28. The method according to claim 12, wherein the plant is a dicotyledonous plant.

29. The method according to claim 14, wherein the plant is a dicotyledonous plant.

30. A genetically modified plant cell, plant, progeny thereof or parts of said genetically modified plant, generated in accordance with the method of claim 4 which comprises a nucleotide sequence as set forth in SEQ ID NO:1, or the complement thereof.

31. A genetically modified plant cell, plant, progeny thereof or parts of said genetically modified plant, generated in accordance with the method of claim 6 which comprises a nucleotide sequence as set forth in SEQ ID NO:1, or the complement thereof.

32. A genetically modified plant cell, plant, progeny thereof or parts of said genetically modified plant, generated in accordance with the method of claim 9 which comprises a nucleotide sequence as set forth in SEQ ID NO:1, or the complement thereof.

33. A genetically modified plant cell, plant, progeny thereof or parts of said genetically modified plant, generated in accordance with the method of claim 12 which comprises a nucleotide sequence as set forth in SEQ ID NO:1, or the complement thereof.

34. A genetically modified plant cell, plant, progeny thereof or parts of said genetically modified plant, generated in accordance with the method of claim 14 which comprises a nucleotide sequence as set forth in SEQ ID NO:1, or the complement thereof.

* * * * *

UNITED STATES PATENT AND TRADEMARK OFFICE
CERTIFICATE OF CORRECTION

| | | |
|---|---|---|
| PATENT NO. | : 7,262,337 B2 | Page 1 of 1 |
| APPLICATION NO. | : 10/433754 | |
| DATED | : August 28, 2007 | |
| INVENTOR(S) | : Mesa et al. | |

It is certified that error appears in the above-identified patent and that said Letters Patent is hereby corrected as shown below:

Column 9, Line 17, "required is nucleotidesequence" should be changed to --required is nucleotide sequence--

Column 16, Line 64, "et al. U.S. Pat. No. 5,122,466)" should be changed to --et al. (U.S. Pat. No. 5,122,466--

Column 21, Line 64, "(smaller intemodal" should be changed to --(smaller internodal--

Column 23, Line 27, "angle of 148.960°" should be changed to --angle of 148.96°--

Signed and Sealed this

Twenty-seventh Day of November, 2007

JON W. DUDAS
*Director of the United States Patent and Trademark Office*